US010517656B2

(12) United States Patent
Biedermann (10) Patent No.: US 10,517,656 B2
(45) Date of Patent: Dec. 31, 2019

(54) MODULAR BONE PLATE AND MEMBER OF SUCH A MODULAR BONE PLATE

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 15/828,149

(22) Filed: Nov. 30, 2017

(65) Prior Publication Data

US 2018/0146994 A1 May 31, 2018

Related U.S. Application Data

(63) Continuation of application No. 14/123,078, filed as application No. PCT/IB2012/053037 on Jun. 15, 2012, now Pat. No. 9,956,016.

(60) Provisional application No. 61/497,972, filed on Jun. 17, 2011.

(51) Int. Cl.
*A61B 17/80* (2006.01)
*A61B 17/70* (2006.01)

(52) U.S. Cl.
CPC ...... *A61B 17/8023* (2013.01); *A61B 17/7059* (2013.01); *A61B 17/80* (2013.01); *A61B 17/8042* (2013.01); *A61B 17/8061* (2013.01)

(58) Field of Classification Search
CPC ..... A61B 17/58; A61B 17/7059; A61B 17/80; A61B 17/8023; A61B 17/8033; A61B 17/8042; A61B 17/8047; A61B 17/8052; A61B 17/8057; A61B 17/8061
See application file for complete search history.

(56) References Cited

U.S. PATENT DOCUMENTS

| 5,484,439 A | * | 1/1996 | Olson ................. A61B 17/746 606/65 |
| 5,520,690 A | | 5/1996 | Errico et al. |
| 8,062,296 B2 | | 11/2011 | Orbay et al. |
| 8,394,098 B2 | | 3/2013 | Orbay et al. |
| 8,394,130 B2 | | 3/2013 | Orbay et al. |
| 2002/0183757 A1 | * | 12/2002 | Michelson ......... A61B 17/7059 606/71 |
| 2004/0074189 A1 | | 4/2004 | Deschenes |

(Continued)

FOREIGN PATENT DOCUMENTS

| CN | 101175449 A | 5/2008 |
| CN | 101557767 A | 10/2009 |

(Continued)

*Primary Examiner* — Zade Coley
*Assistant Examiner* — Amy R Sipp
(74) *Attorney, Agent, or Firm* — Gordon & Jacobson, P.C.

(57) ABSTRACT

A member of a modular bone plate is provided, the member comprising a top surface defining a top plane; a bottom surface defining a bottom plane; a connection portion including a hole with a center axis that intersects the top plane and the bottom plane; wherein a first portion of the edge of the hole is provided with a projection forming a first free end of the member and wherein a second portion of the edge of the hole is provided with a groove that is configured to accommodate a projection of a connection portion of a second member of the modular bone plate. Furthermore, a modular bone plate having at least two such members is provided.

11 Claims, 12 Drawing Sheets

(56) References Cited

U.S. PATENT DOCUMENTS

| | | |
|---|---|---|
| 2004/0102778 A1 | 5/2004 | Huebner et al. |
| 2004/0204713 A1* | 10/2004 | Abdou ............... A61B 17/8004 606/71 |
| 2006/0100625 A1 | 5/2006 | Ralph et al. |
| 2006/0229610 A1 | 10/2006 | Piehl |
| 2006/0276794 A1* | 12/2006 | Stern .................. A61B 17/7059 606/71 |
| 2007/0276383 A1 | 11/2007 | Rayhack |
| 2008/0039847 A1 | 2/2008 | Piper et al. |
| 2009/0036930 A1 | 2/2009 | Allison |
| 2009/0082813 A1 | 3/2009 | Long et al. |
| 2010/0121328 A1 | 5/2010 | Reitzig et al. |
| 2010/0274248 A1 | 10/2010 | Overes et al. |
| 2012/0029579 A1* | 2/2012 | Bottlang ............. A61B 17/8042 606/315 |
| 2014/0100572 A1 | 4/2014 | Biedermann |

FOREIGN PATENT DOCUMENTS

| | | |
|---|---|---|
| DE | 102009055826 A1 | 5/2011 |
| JP | 2006-507898 A | 3/2006 |
| WO | WO2004/049903 A2 | 6/2004 |
| WO | WO2006/102081 A1 | 9/2006 |
| WO | WO2008/057861 A2 | 5/2008 |
| WO | WO2009/105066 A1 | 8/2009 |
| WO | WO2012/172517 A1 | 12/2012 |
| WO | WO2012/172519 A1 | 12/2012 |

* cited by examiner

MODULAR BONE PLATE AND MEMBER OF SUCH A MODULAR BONE PLATE

CROSS-REFERENCE TO RELATED APPLICATIONS

This application is a continuation of U.S. Ser. No. 14/123,078, filed Nov. 27, 2013, which claims benefit under 35 USC § 371 to PCT/IB2012/053037, filed Jun. 15, 2012, which claims priority to U.S. Provisional Application No. 61/497,972, filed on Jun. 17, 2011, all of which are hereby incorporated by reference in their entireties.

FIELD OF THE INVENTION

The invention relates to a modular bone plate and to a member of such a modular bone plate.

BACKGROUND OF THE INVENTION

Various shapes and types of bone plates to be used for osteosynthesis of fragmented bones and for stabilization of bones are known. The shape, size and type of a bone plate are usually adapted to the bones that shall be stabilized or immobilized. Hence, a large inventory of bone plates is typically necessary to be able to treat many different kinds of fractures or other defects at different locations.

There exist also modular bone plate systems that allow construction of a bone plate adapted to a specific application and to the individual patient by combining single members to form a whole bone plate. For example, US 2009/0082813 A1 describes a modular bone plating system including a plurality of bone plates including a male coupling portion, a female coupling portion and a shaft extending between the male coupling portion and the female coupling portion, wherein each of the male coupling portions of each of the plurality of bone plates is configured to couple with each of the female coupling portions of each of the other of the plurality of bone plates.

U.S. Pat. No. 5,484,439 describes a modular femur fixation device. The device comprises an upper side plate with a widened head and an angled barrel, and a lower side plate adapted to be engaged with the upper side plate in a tongue and groove configuration.

SUMMARY OF THE INVENTION

It is the object of the invention to provide a modular bone plate and a member of such a modular bone plate that is simplified in terms of handling and manufacturing while exhibiting a strength that is comparable to single part bone plates.

The object and further developments are addressed by the various embodiments of the invention.

The modular bone plate is assembled by connecting at least two members of the modular bone plate at their respective connection portions such that the projection of the connection portion of a first member is introduced into the groove of a connection portion of the second member. In the assembled configuration the holes of both connection portions are arranged concentrically, on top of each other. The assembly is quickly and easily performed and the resulting construct is prevented from disassembling by the form locking connection between the projection and the groove. Hence, the surgeon can take the pre-assembled bone plate and place it on to the bone parts or fragments or bones that need to be connected or stabilized without using further elements or tools for keeping together the bone plate members.

Due to modularity, lower inventory may be required and it may be possible to reduce the bone plate set price. Also, custom plates may be assembled to meet specific patient needs, on a case-by-case basis. A great variety of modular bone plate members can be provided and the members can be combined in various manners. For example, the modular bone plate can be used with bone anchors with spherical heads that allow for an angled configuration of the bone anchor relative to the bone plate, with set screws, with plugs to close the holes etc. or with combinations thereof. This opens a great field of clinical applications. Because of this easy and secure assembly and the resulting strong construct, the surgeon can select different modular pieces and assemble a custom bone plate directly in the operating room, used for a specific application.

Modifications of the design of the modular bone plate member allow the surgeon to connect the members to form an angled configuration with a variable angle that can be selected by the surgeon. Further modifications allow for modular bone plate members of different thicknesses to be combined to form bone plate constructs of variable thickness."

BRIEF DESCRIPTION OF THE DRAWINGS

Further features and advantages will become apparent from the description of embodiments and means of the accompanying drawings.

In the drawings:

FIG. 2 a): shows a perspective exploded view of the modular bone plate according to the first embodiment.

FIG. 2 b): shows a perspective view from the bottom of the first plate member of the modular bone plate of FIG. 1.

FIG. 19 a) to c): shows a top view of a modular bone plate according to a second embodiment in different angular positions of the bone plate members relative to each other.

FIG. 20 a) to e): shows a perspective view of the modular bone plate according to a modification of the second embodiment in different angular relationships of the bone plate members.

DETAILED DESCRIPTION OF THE INVENTION

As shown in FIGS. 1 to 4, the modular bone plate according to the first embodiment includes at least a first member 1 and a second member 2 that are to be connected to each other. The first member is shaped in the form of an elongated plate and comprises a top surface 1 a and a bottom surface 1 b that are substantially parallel to each other and define the height of the first member 1. The first member 1 further has a first free end 1 c and a second free end 1 d opposite to the first free end 1 c. Furthermore, the first member 1 comprises a connection portion 10 that serves for connecting the first member 1 to the second member 2. The connection portion 10 extends from the second free end 1 d to a distance therefrom in a longitudinal direction of the first member 1. It comprises a hole 11 that is a through-hole as can be seen in particular in FIGS. 2 a) and 2 b). The edge of the hole 11 that extends to the second free end 1 d is substantially semi circular and comprises a projection 12 that forms the free end 1 d. The projection 12 is located at a distance, in particular a small distance, from the bottom surface 1 b at substantially the middle of the height between the top surface 1 a and the bottom surface 1 b. Further, the connection portion 10 comprises a recess by means of which an upper portion adjacent the top surface 1 a of the first member is cut out. The recess extends into the first member to a distance from the edge of the hole 11 so as to form a groove 13. The groove 13 has a distance from the top surface 1 a that corresponds substantially to the distance of the projection 12 from the bottom surface 1 b. The size and the shape of the grooves correspond to the size and shape of the projection 12. Hence, the groove 13 is semi-circular. At both free ends of the groove 13 a substantially rectangular recess is provided, as can be seen in particular in FIGS. 2 a and 2 b.

Figure 1:
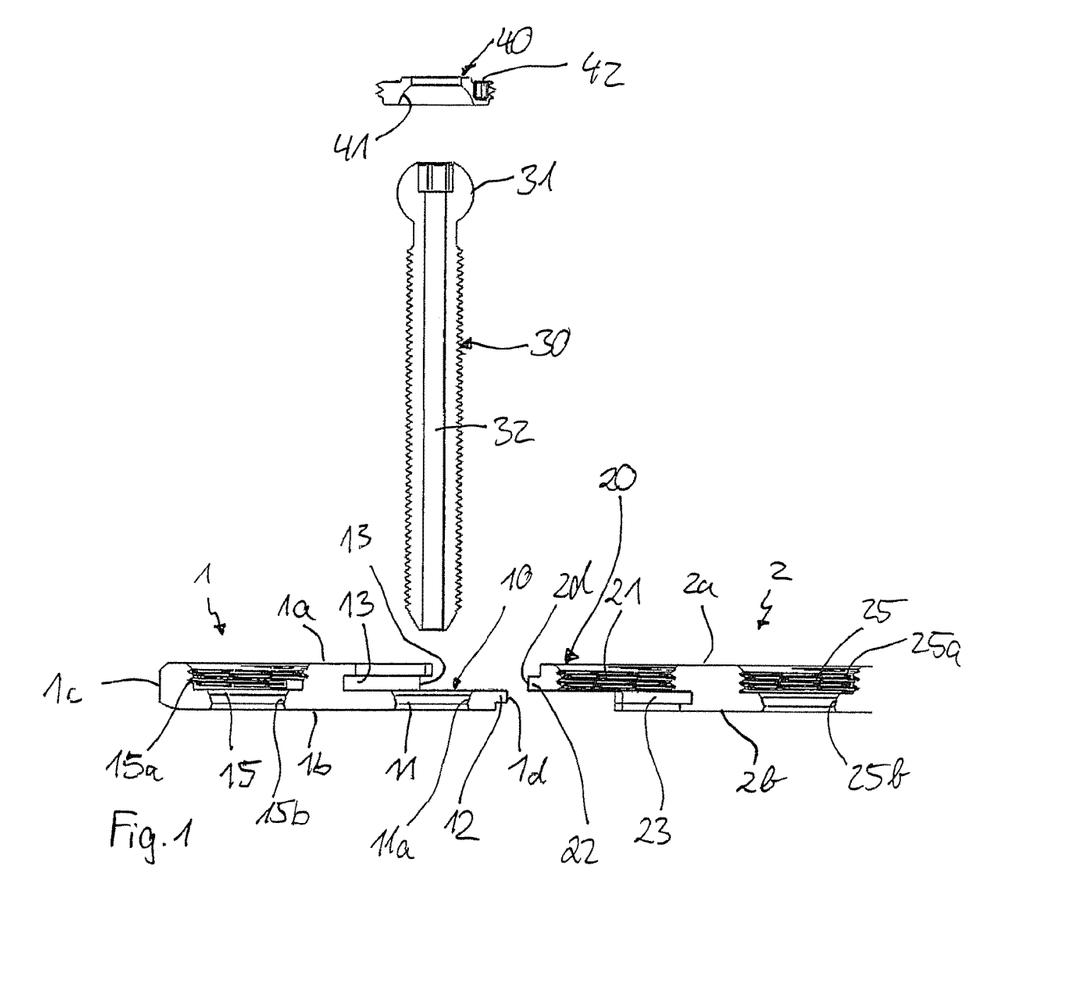
FIG. 1: shows a schematic exploded cross-sectional view of a first embodiment of the modular bone plate with a bone anchor and a cap to secure the bone anchor.
Figures 2A, 2B:
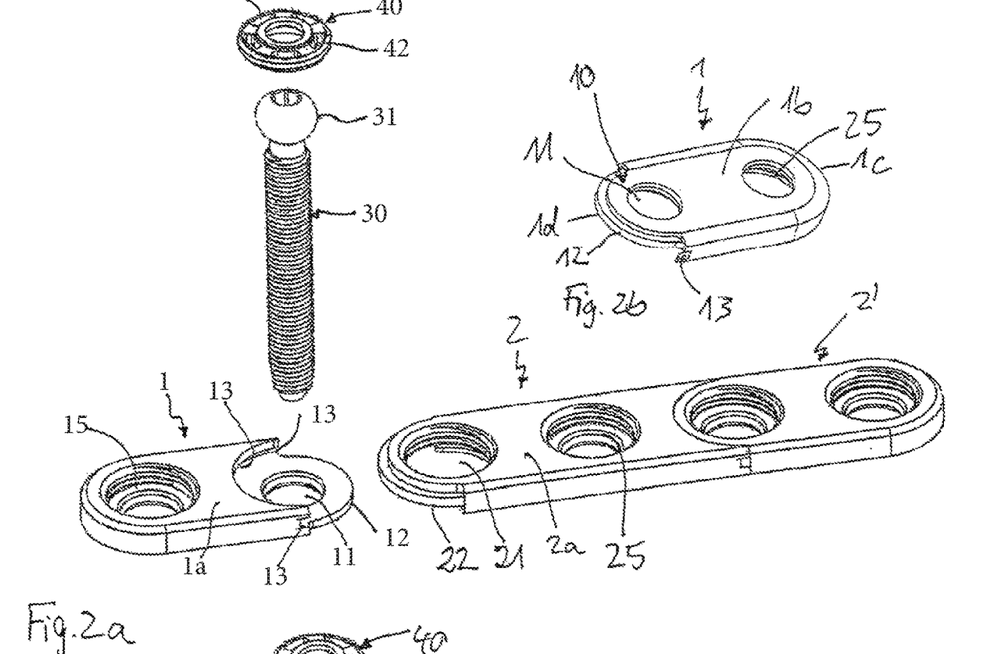

The hole 11 comprises a section 11 a that is shaped as a segment of a sphere with the smaller diameter oriented towards the bottom surface 1 b. This hollow spherically-shaped portion 11 a serves as a seat for a spherically-shaped head 31 of a bone anchor 30.

The first member 1 comprises a further hole 15 extending from the top surface 1 a to the bottom surface 1 b. The hole 15 has a first portion 15 a that is at least partially threaded and is configured to receive a locking cap 40 to be placed onto a spherical head of another bone anchor. The hole 15 further comprises a spherically-shaped portion 15 b for receiving the spherical head of the bone anchor.

The second member 2 is also formed as an elongated plate and comprises a top surface 2 a and a bottom surface 2 b. The distance between the top surface 2 a and the bottom surface 2 b defines the height of the member 2 that is identical to the height of the plate member 1. The second member 2 has a first free end (not shown in FIG. 1) and an opposite second free end 2 d.

Similar to the first member 1, the second member 2 has a connection portion 20 that is to be connected to the connection portion 10 of the first member 1. The connection portion 20 comprises a hole 21. The edge of the hole 21 extending to the second free end 2 d comprises a projection 22 that is semi-circular and sized and arranged so that it fits into the groove 13 of the first connection portion 10. Further, the second member 2 comprises a recess that cuts out a portion from the bottom surface 1 b up to substantially the middle of the height of the member 2 and extends to the edge of the hole in a direction to the first end 2 c so as to form a groove 23. The groove 23 is sized and arranged to receive the projection 12 of the first member 1. The hole 21 is at least partially threaded and configured to receive the cap 40 that secures the head of the bone anchor 30.

The second member 2 comprises at least a second hole 25 with an at least partially threaded portion 25 a adjacent the top surface 2 a and a spherically-shaped portion 25 b in the lower part to receive a spherical head of another bone anchor.

In one embodiment, the modular bone plate includes a third piece, such as a cap or screw, for example, to connect and/or hold (compress and/or lock) the two members (the first member 1 and the second member 2) together. The third piece functions to maintain the assembly of the plate, after it is placed on the bone.

Figure 3:
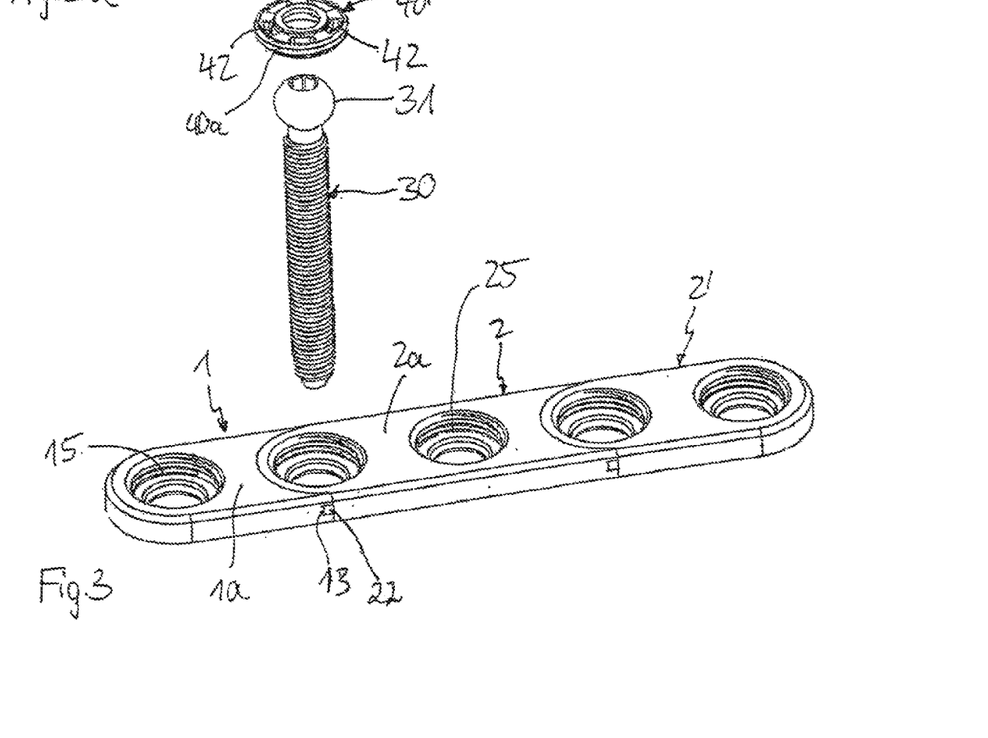
FIG. 3: shows a perspective exploded view of the modular bone plate according to the first embodiment wherein the bone plate members have been connected.
Figure 4:
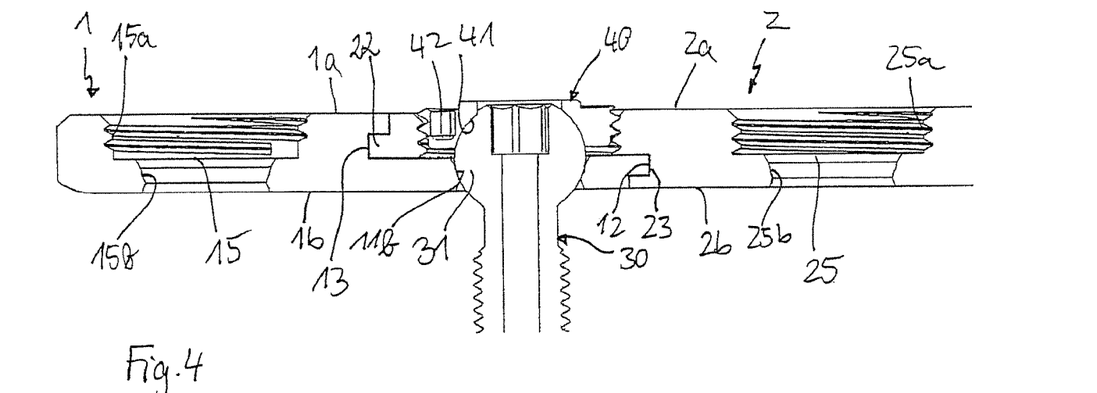
FIG. 4: shows a cross-sectional view of the modular bone plate according to the first embodiment wherein the bone plate members have been connected and the bone anchor and the cap have been inserted.

The assembly of the modular bone plate will now be described with reference to FIGS. 3 and 4. To connect the members 1 and 2 to each other, the members are oriented with their second free ends 1 d, 2 d facing towards each other as shown in FIG. 1. Then, the projection 22 of the second member is inserted into the groove 13 of the first member. Because of the substantially symmetrical design, the projection 12 of the first member is simultaneously introduced into the groove 23 of the second member 2. When the projections are fully introduced into the grooves, they abut against the inner wall of the grooves and the holes 1 1and 21 overlap. The bottom surface 1 b of the first member and the bottom surface 2 b of the second member are substantially flush as can be seen in particular in FIG. 4. Due to the recess resulting from groove 13 of the first member, the side faces of the plate members are substantially flush as shown in FIG. 3. It is possible to dimension the groove 13 of the first member substantially semi-circular so that the side faces of the plate members are substantially flush as shown in FIG. 3.

The dimensions of the connection portions are such that once connected, the projections fit tightly into the grooves such that the assembled bone plate can be placed onto the bone without the members falling apart. Once the modular bone plate has been placed onto the bone, the bone anchor 30 can be inserted so that the spherical head 31 is seated in the spherically-shaped portion 15 b of the hole 11. The bone anchor 30 may have a coaxial through hole 32 for injection of substances or bone cement and/or for guiding through a guide wire that may be used to place the bone anchor into the bone. The bone anchor 30 may assume different angular positions with respect to the plate because the head 31 is accommodated in the spherically-shaped portion 15 b in the manner of a ball and socket joint.

The locking cap 40 has a threaded outer surface 40 a and a spherically-shaped recess 41 oriented towards the spherical head 31 of the bone anchor 30. On the opposite side, the cap comprises a plurality of pockets 42 for engagement with a driver. The locking cap 40 is screwed into the at least partially threaded hole 21 to secure the bone anchor in the plate and prevent backing out of the bone anchor.

The connection between the connection portions provides a substantially uniform load distribution between the two plate members.

Figure 5:
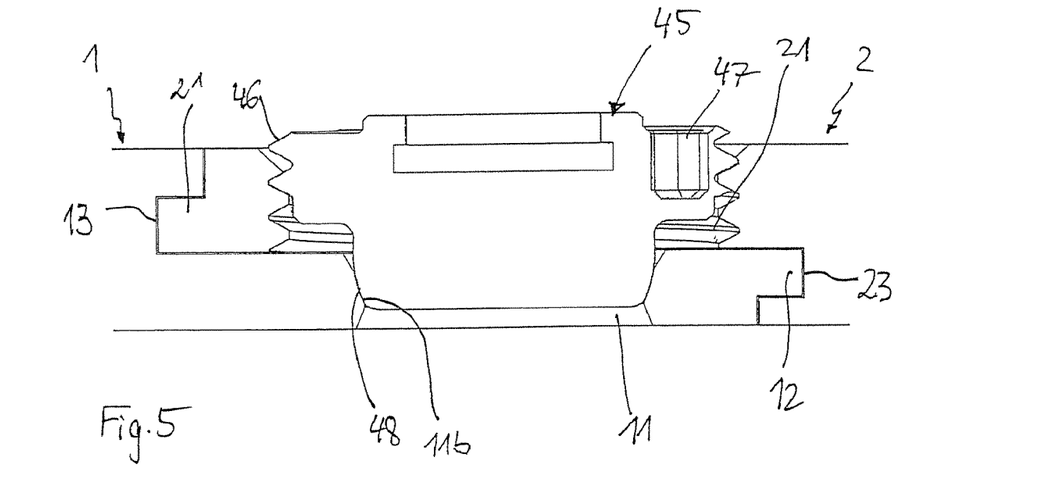
FIG. 5: shows an enlarged cross-sectional view of the modular bone plate according to the first embodiment with an inserted plug to close the hole.

In FIG. 5 the first member 1 and the second member 2 are assembled and the holes 11, 21 are closed by a closure plug 45 that is similar to the locking cap 40 in that it has a threaded section 46 cooperating with the threaded hole 21 and pockets 47 for a driver. In the lower part, the closure plug 45 has a spherically-shaped section 48 that fits into the spherically-shaped portion 15 b of the hole 11. By means of this, two members can be connected without using a bone anchor.

Figure 6:
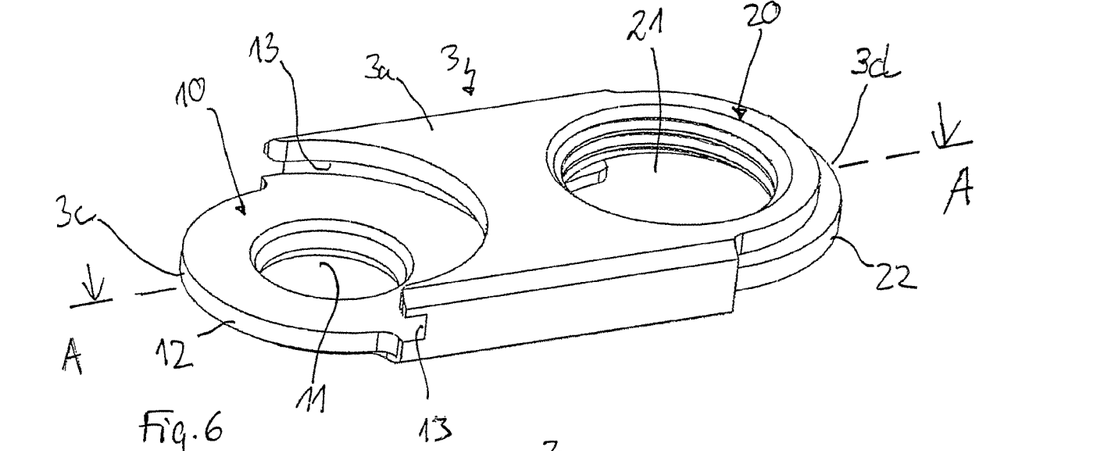
FIG. 6: shows a perspective view from the top of a connector member of the modular bone plate according to the first embodiment.
Figure 7:
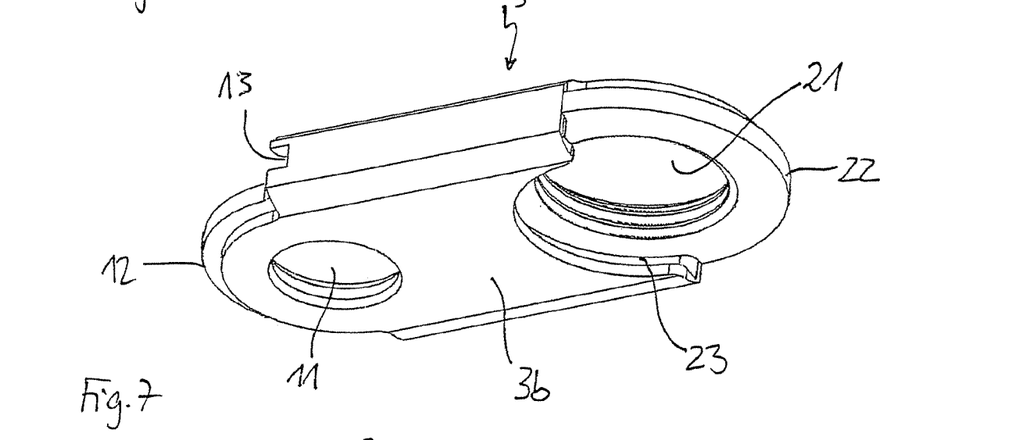
FIG. 7: shows a perspective view from the bottom of the connector member according to FIG. 6.
Figure 8:
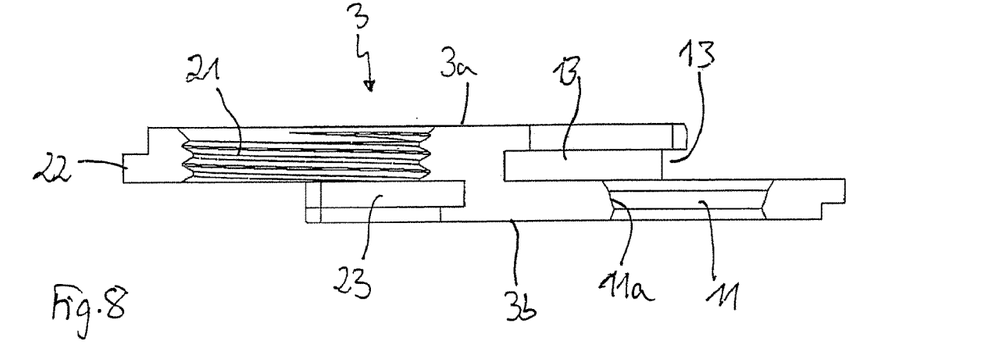
FIG. 8: shows a schematic cross-sectional view of the connector member according to FIG. 6, wherein the cross-section is taken along line A-A in FIG. 6.

FIGS. 6 to 8 show a further member of the modular bone plate. The member 3 is a connector member that has a top surface 3 a, a bottom surface 3 b, a first free end 3 c and a second free end 3 d. The connector piece comprises two connection portions 10, 20. The first connection portion 10 is arranged at the first free end 3 c and the second connection portion 20 is arranged at the second free end 3 d. The first connection portion 10 is identical to the first connection portion 10 of the first member 1 and the second connection portion 20 is identical to the second connection portion 20 of the second member 2 described above. Therefore, all details of the first and second connection portion 10, 20 are indicated with the same reference numerals as for the first member 1 and the second member 2. The description thereof will not be repeated.

The connector member 3 serves as an intermediate member that may connect to other members of the type of the first member 1 and the second member 2. The distance between the first and the second connection portion may vary so that a plurality of connector pieces in the form of the third member 3 can be provided that have different length.

Figure 9:
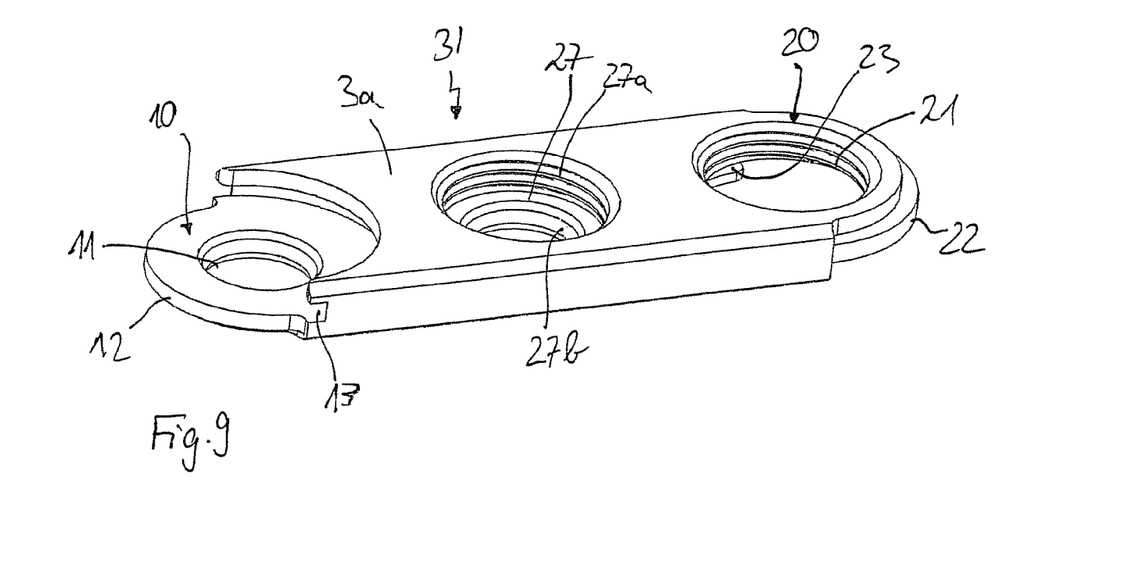
FIG. 9: shows a perspective view from the top of a second member of the modular bone plate according to the first embodiment.

FIG. 9 shows a modified third member 3' that differs from the third member 3 shown in FIGS. 6 to 8 in that a further hole 27 is provided between the first connection portion 10 and the second connection portion 20. The hole 27 has an at least partially threaded portion 27 a adjacent the top surface 3 a and a spherically-shaped portion 27 b for accommodating the spherical head 31 of a bone anchor that is similar to the bone anchor 30. It may be envisaged that several additional holes can be provided between the first connection portion 10 and the second connection portion 20.

Figure 10:
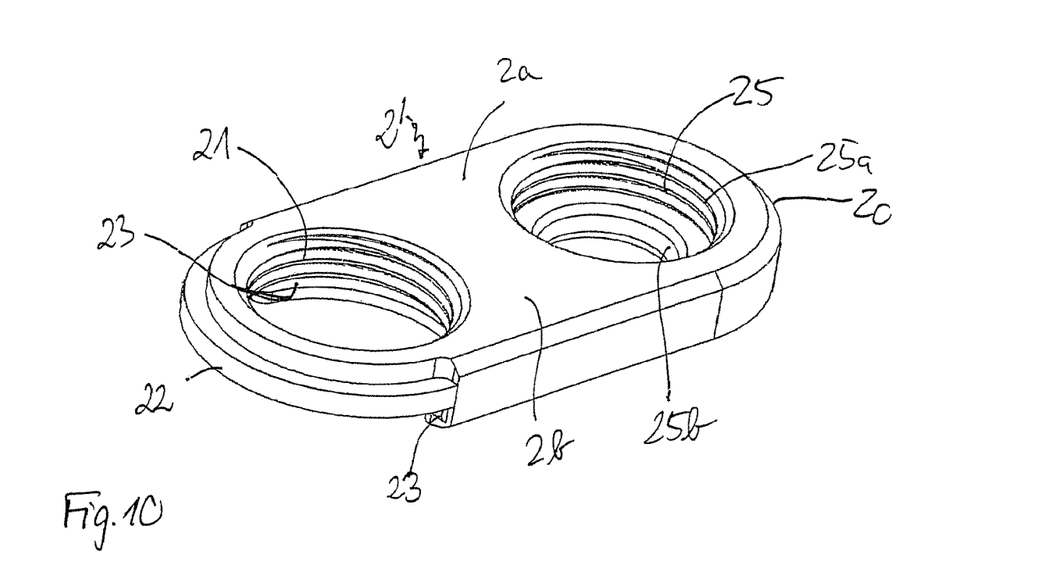
FIG. 10: shows a perspective view from the top of a third member of the modular bone plate according to the first embodiment.

FIG. 10 shows an end member 2', similar to the first member 1. Preferably, the end member has a rounded free end 2 c.

Figure 11:
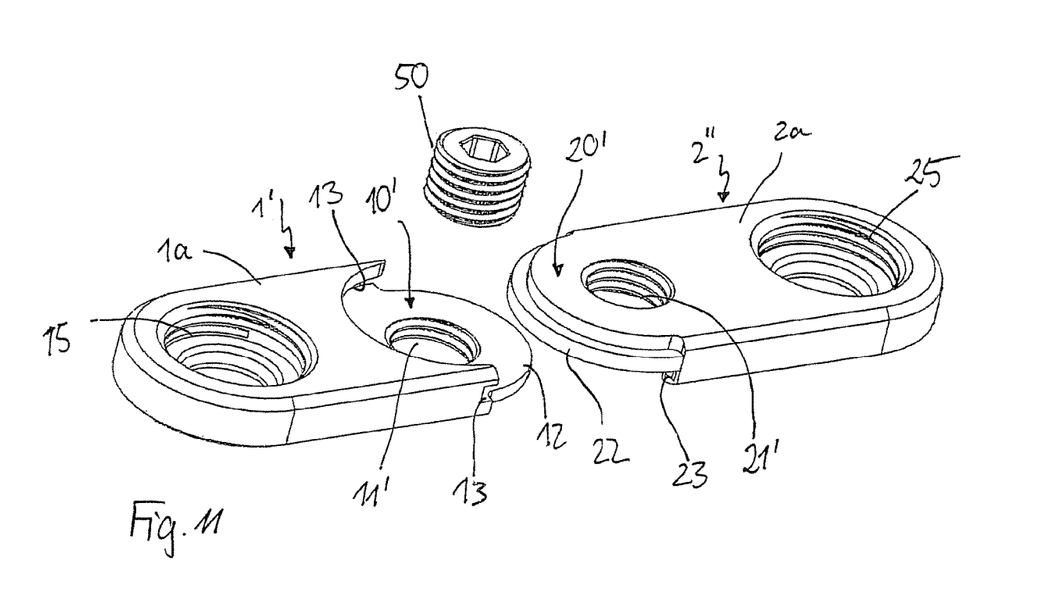
FIG. 11: shows a perspective exploded view of the modular bone plate according a modification of the first embodiment.
Figure 12:
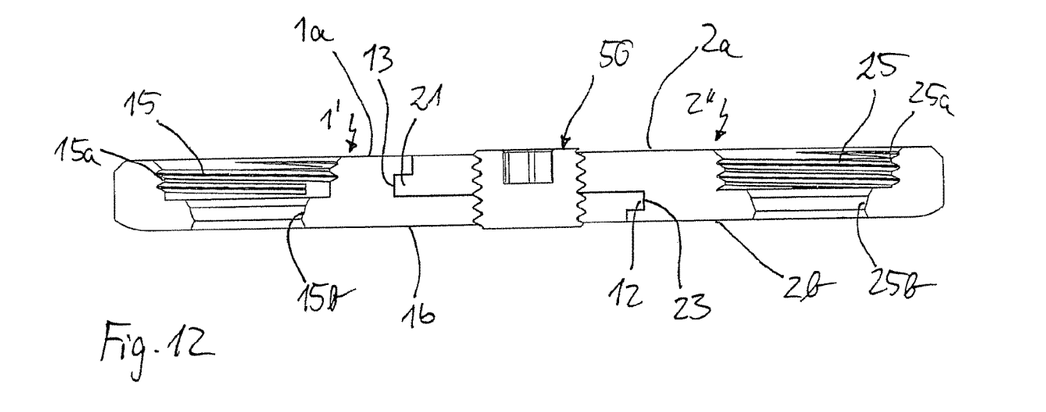
FIG. 12: shows a schematic cross-sectional view of the assembled modular bone plate according to FIG. 11.

FIGS. 11 and 12 show a further modification of the modular bone plate according to the first embodiment. The plate members 1', 2" differ from the plate members 1 and 2' described before in the connection portion 10', 20', respectively. The connection portions 10', 20' each have a threaded hole of the same size. When the plate members 1', 2" are connected to each other a set screw 50 can be screwed-in to connect the plate members. All details that are identical to that of the previous embodiments are indicated with the same reference numerals and the description thereof is not repeated.

Figure 13:
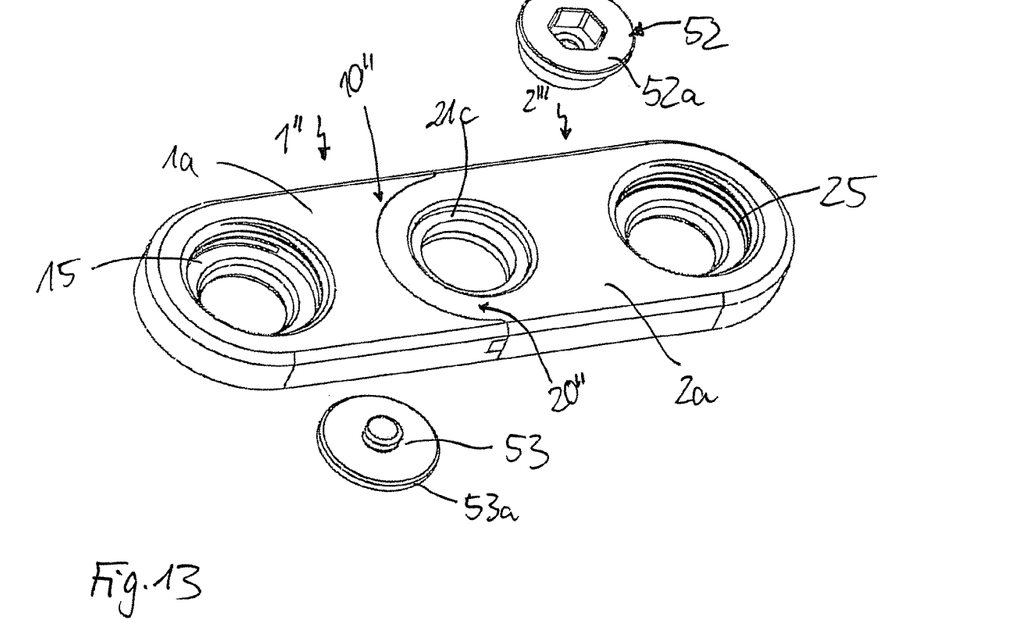
FIG. 13: shows a perspective partially exploded view of a further modification of the modular bone plate according to the first embodiment.
Figure 14:
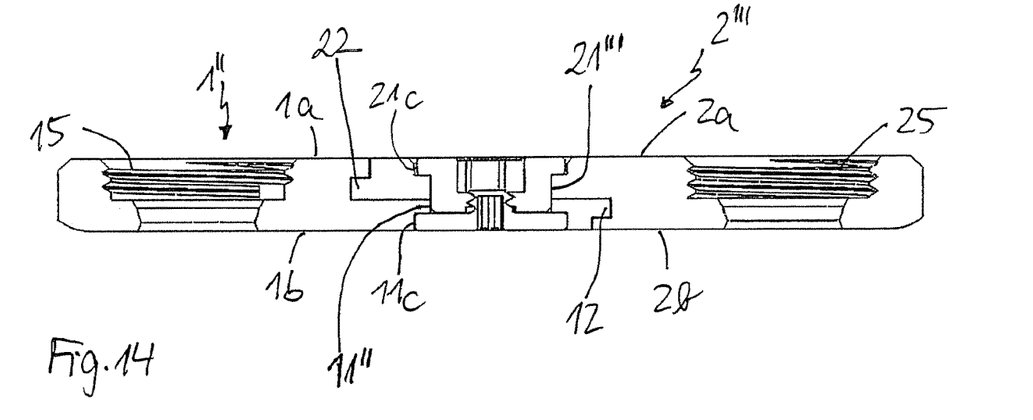
FIG. 14: shows a schematic cross-sectional view of the assembled modular bone plate according to FIG. 13.

FIGS. 13 and 14 show a further modification of the modular bone plate shown in FIGS. 11 and 12. The plate members 1" and 2' comprise connection portions 10" and 20"". The holes 11" and 21" are threadless and comprise recesses 11 c, 21 c for accommodating a flange 52 a of nut 52 and a flange 53 a of a screw 53, respectively. The nut 52 and the screw 53 cooperate to fix the connection as shown in FIG. 14.

Figure 15:
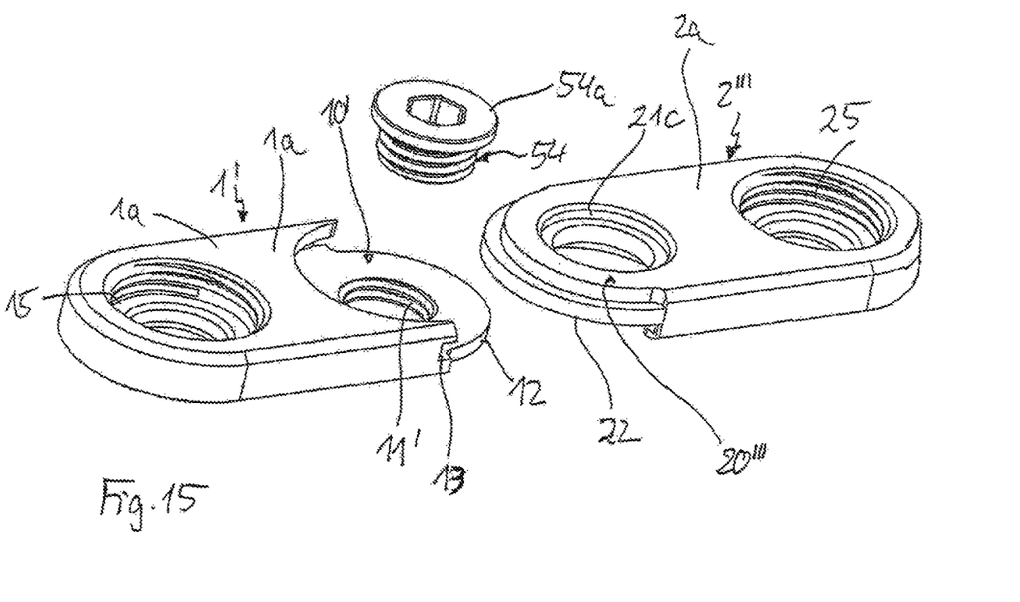
FIG. 15: shows an exploded perspective view of a further modification of the modular bone plate according to the first embodiment.
Figure 16:
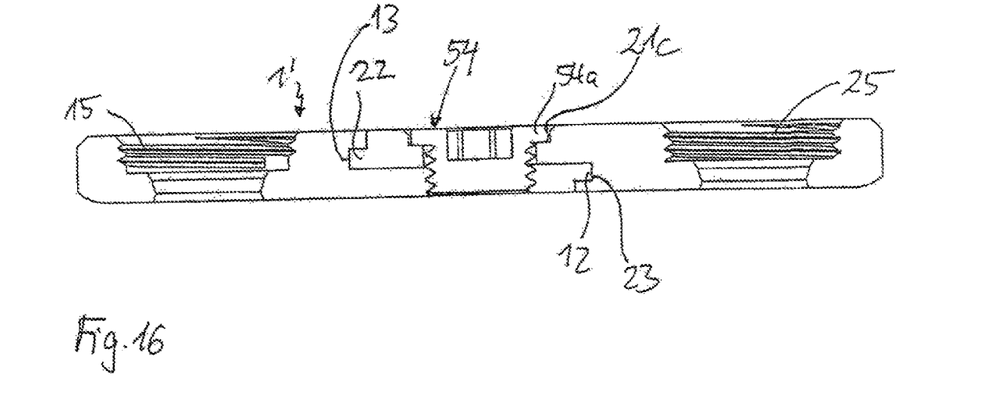
FIG. 16: shows a schematic cross-sectional view of the modular bone plate of FIG. 15 in an assembled state.

FIGS. 15 and 16 show a further modification of the plate members and the connection thereof. The plate member 1' is substantially identical to the first plate member 1' of FIGS. 11 and 12. The plate member 2''' corresponds substantially to the plate member 2''' of FIGS. 13 and 14. Hence, a screw 54 with a flange 54 a can be used to connect the plate members together as shown in FIG. 16.

Figure 17:
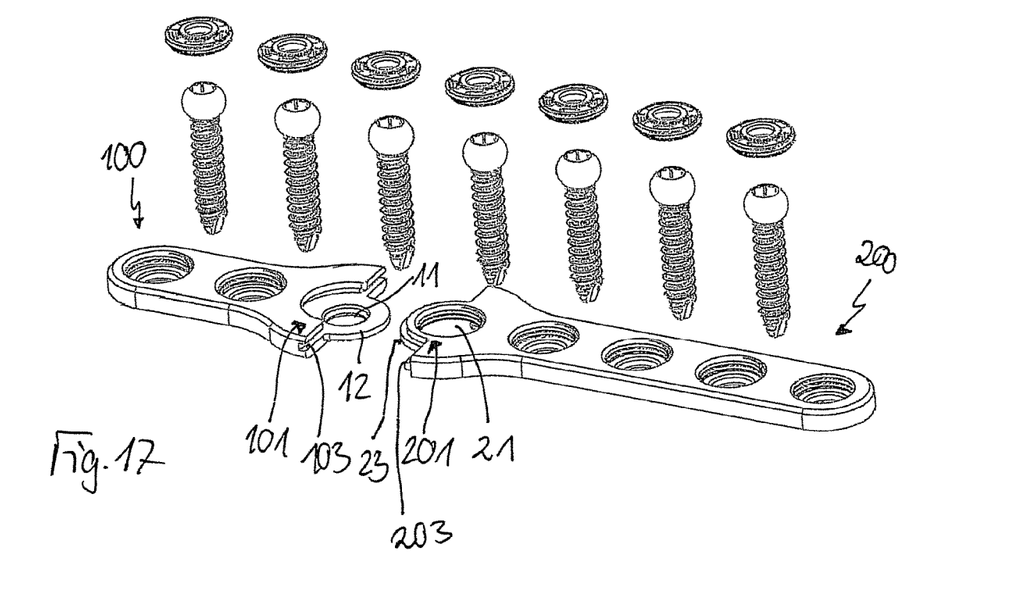
FIG. 17: shows an exploded perspective view of a further modification of the modular bone plate according to the first embodiment.
Figure 18:
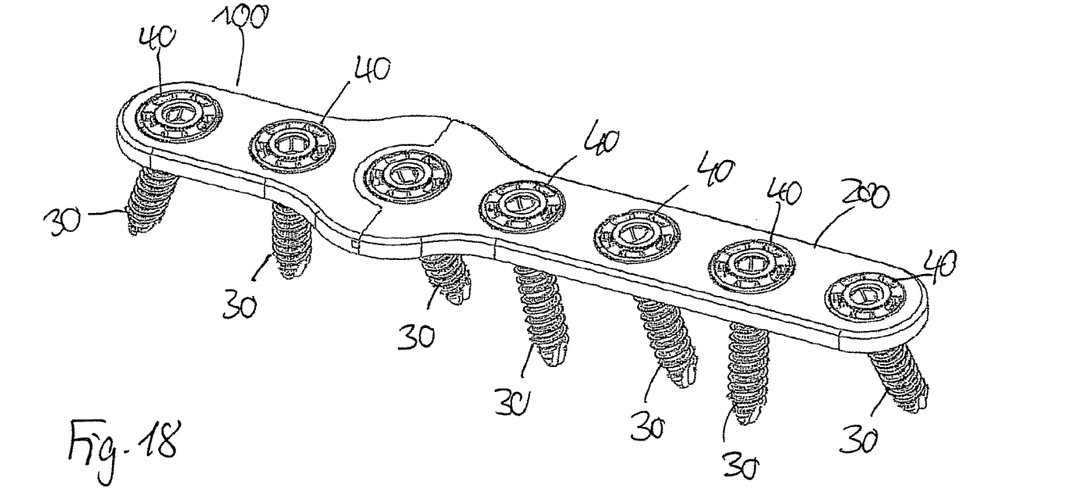
FIG. 18: shows a perspective view from the top of the modular bone plate of FIG. 17 in an assembled state.

A further modification of the first embodiment is shown in FIGS. 17 and 18. The first plate member 100 has a first connection portion 101 and the second plate member 200 has a second connection portion 201. The first connection portion 101 and the second connection portion 201 have a greater width than in the previous embodiments. The width may be greater than the remainder of the first member 100 and the second member 200. However, dependent on the application, the width may also be the same over the length of the plate member. On both sides of the projection 12 in the width direction, there is a groove 103 that extends substantially perpendicular to the length direction of the plate member 100. The second plate member 200 has a corresponding projection 203 extending perpendicular to the length direction of the plate member 200 that cooperates with the groove 103. Hence, the groove 13 is enlarged by the groove 103 and the projection 23 is enlarged by the projection 203. As shown in FIG. 18 this provides larger contact area of the two plate members 100, 200 and simultaneously a greater width of the bone plate. This provides a strengthened connection.

Figure 19:
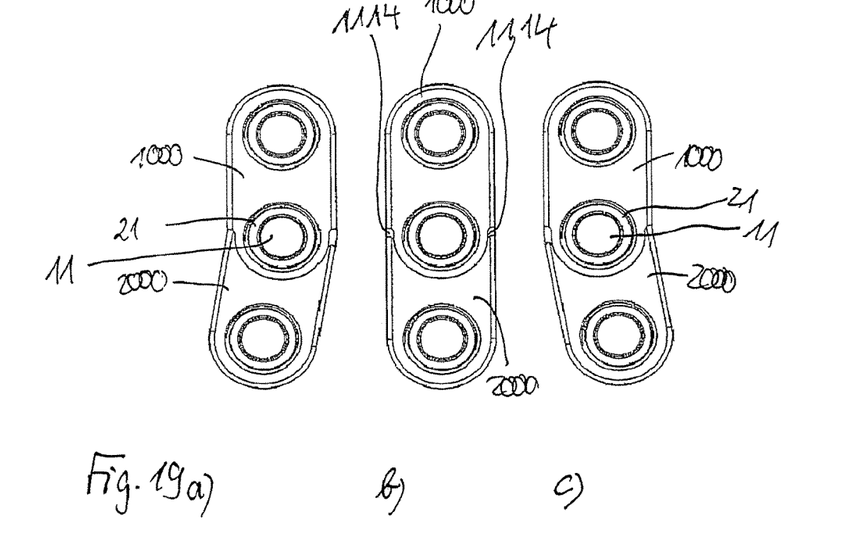

FIG. 19 shows a still further embodiment of the modular bone plate. The first plate member 1000 and the second plate member 2000 can assume an angled position with respect to each other as shown in FIGS. 19 a) and 19 c). To achieve this, first plate member 1000 has a recess 1114 at both ends of the groove 13 so that, when the second plate member 2000 is inserted with its projection 22 into the groove 13, there is a gap between the end of the groove 13 and the second plate member 2000 as can be seen in particular in FIG. 19 b). This allows for pivoting of the second plate member 2000 with respect to the first plate member 1000 around the axes of the holes 11, 21 to a certain angle that may be up to around 10° or 15° (soft angle).

Figure 20:
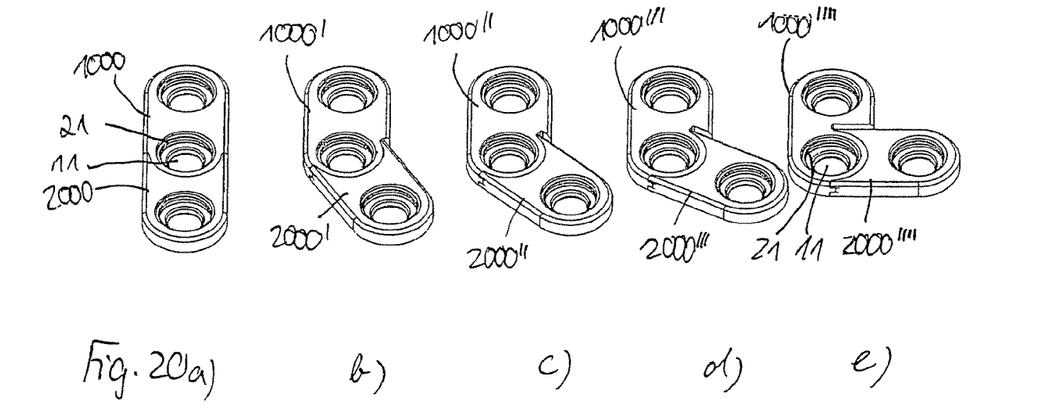

In a still further embodiment shown in FIGS. 20 *a*) to 20 *e*) the groove 13 in the first plate member 1000 is provided at a rotated position with respect to the axes of the holes 11, 21. Positions between around 15°, shown in FIGS. 20 *b*) and 90° in FIG. 20 *e*) are possible (hard angle). Because the groove is part of the first connection member 1000 the angle is fixed and can not be changed as in the embodiment of FIG. 19. Those having ordinary skill in the art will appreciate that a combination of hard and soft angles may be utilized, according to the above.

Figure 21:
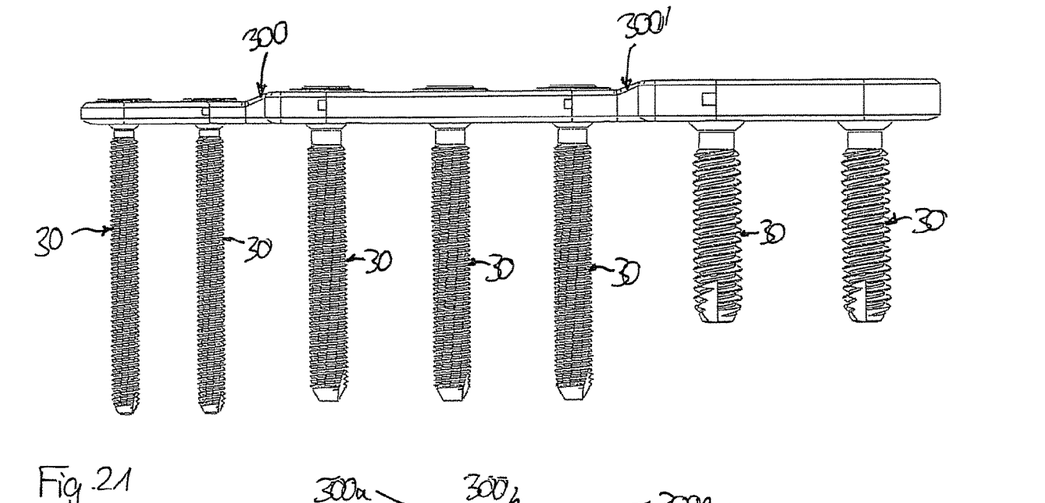
FIG. 21: shows a third embodiment of the modular bone plate in side view.
Figure 22:
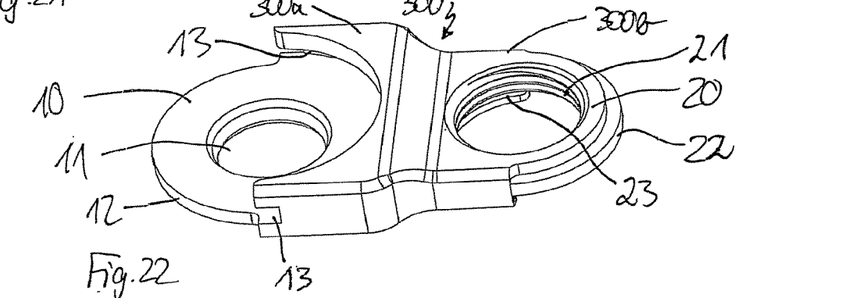
FIG. 22: shows a perspective view from the top of a member of the bone plate according to the third embodiment.
Figure 23:
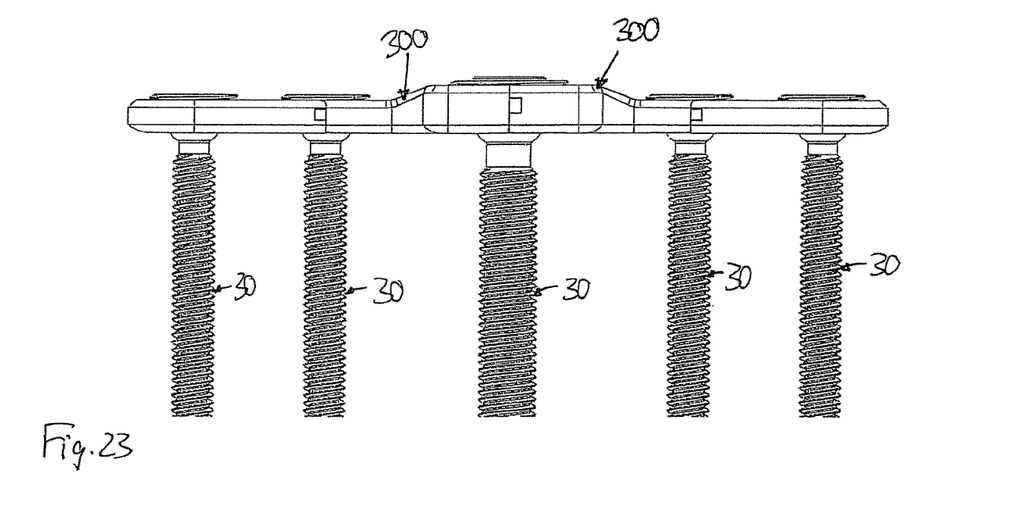
FIG. 23: shows a further modification of the modular bone plate according to the third embodiment.

In a further embodiment shown in FIGS. 21 to 23 a modular bone plate can have different thicknesses along the length of the modular bone plate. To achieve this, a connector piece 300 as shown in FIG. 22 is provided that has a first portion 300 *a* that comprises the first connection portion 10 and a second portion 300 *b* that comprises the second connection portion 20. The bottom surface of portions 300 *a* and 300 *b* is on the same level. However, the thickness of the portion 300 *a* is greater than the thickness of the portion 300 *b*. Hence, the connector piece can be used to connect plate members having different thicknesses. FIG. 21 shows a cascaded configuration wherein the thickness is increasing from one end to the other end of the modular bone plate in steps and FIG. 23 shows an application wherein the thickness is greatest in the center part of the bone plate.

Figure 24:
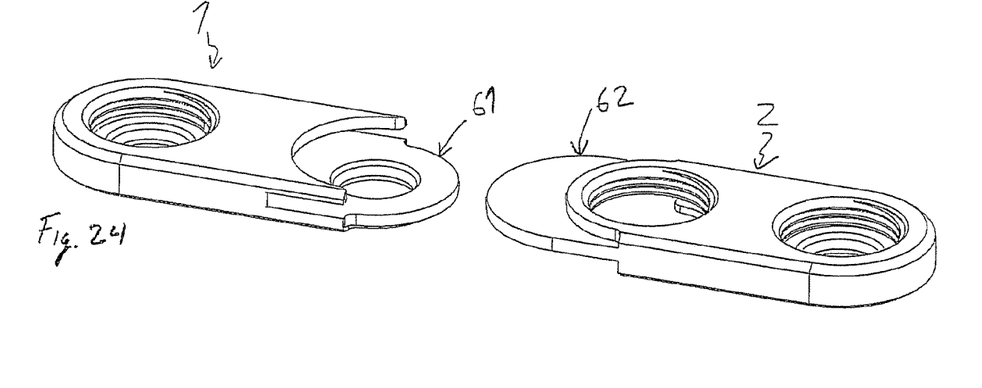
FIG. 24: shows a fourth embodiment of the modular bone plate in perspective view from the top and in a disassembled state and without a connector piece.
Figure 25:
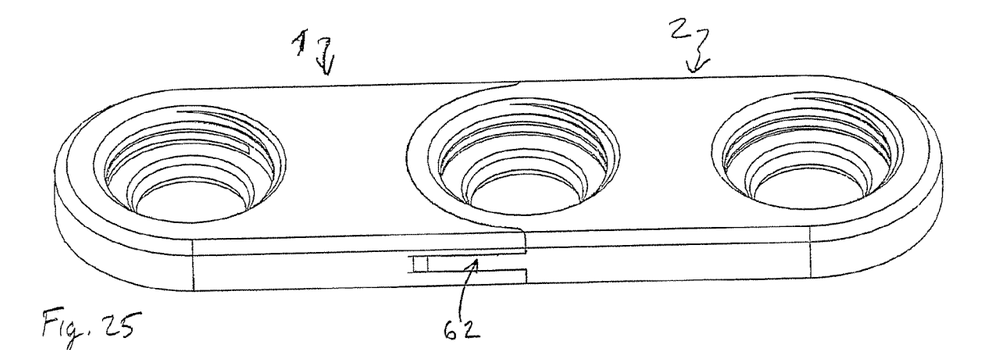
FIG. 25: shows a perspective view of the modular bone plate of the fourth embodiment in an assembled state and without a connector piece.
Figure 26:
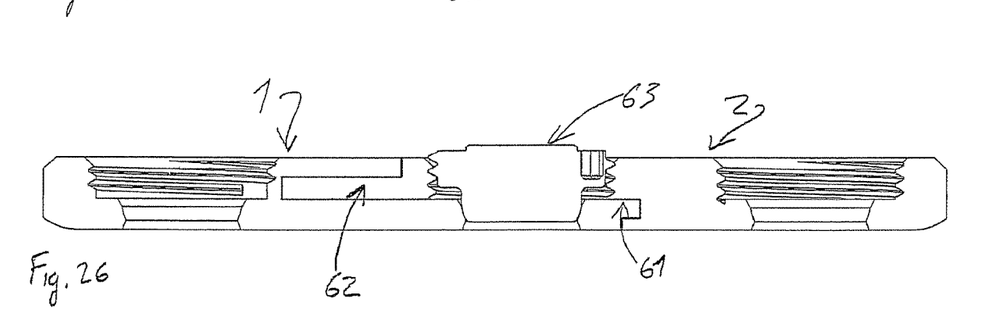
FIG. 26: shows a longitudinal section view of the modular bone plate of the fourth embodiment in an assembled state and with a connector piece.

Referring now to FIGS. 24-26, schematic diagrams of a further embodiment are shown in which longer flanges or tongues 61 and 62 are provided. The longer flanges may enable more stable connections between members 1 and 2, due to better distribution of forces, for example. In FIG. 26, a locking cap 63 is shown for fastening together members 1 and 2. The embodiment described with respect to FIGS. 24-26 may otherwise function similarly to earlier-described embodiments.

The members of the modular bone plate can be made of any bio-compatible material. Preferably, the members are made of titanium, stainless steel, bio-compatible alloys or bio-compatible plastic materials, such as, for example PEEK (polyetheretherketone). The members can be made all of the same material or can be made of different materials so that the modular bone plate has different materials in one portion thereof compared to another portion.

It should be clear from the above that plate members can be designed in many configurations and are not limited to the specific embodiments shown above. For example, plate members can have less or more holes as shown. The contour of the plate members may vary. The holes may be threaded and provided with spherically-shaped sections for an angled insertion of the bone anchor or may have only threads for straight and fixed angle insertion of the bone anchor. The holes may even have an axis that is not perpendicular to the top and the bottom surface but includes an angle with the top and the bottom surface. The features of all the embodiments described above can be combined among each other to provide a specific plate member needed for a specific application. Therefore, the necessary inventory can be reduced.

By means of the modularity and the simplicity of handling while ensuring sufficient strength, the field of applications of the modular bone plate is enlarged. Plate members can be produced in all sizes so that the modular bone plate can be used in pediatric orthopedics, cervical spine surgery, hand surgery, long bone treatment and many other applications.

What is claimed is:

1. A modular bone plate system comprising:
a first plate member comprising a top surface defining a top plane, a bottom surface defining a bottom plane, and a first connection portion defining a first hole with a first center axis that intersects the top plane and the bottom plane;
a second plate member comprising a top surface defining a top plane and a bottom surface defining a bottom plane, and a second connection portion defines a second hole with a second center axis that intersects the top and bottom planes of the second member, wherein the first connection portion is pivotably couplable relative to the second connection portion such that the first hole is alignable over the second hole,
wherein a first part of the first connection portion of the first plate member comprises a wall that extends around and faces away from the first center axis of the first hole, and a projection that extends away from the wall of the first part of the first plate member and forms a first free end of the first plate member, wherein a second part of the first connection portion of the first member comprises a wall that is spaced apart from the first hole and extends around and faces towards the first center axis of the first hole, and wherein a groove is formed in the wall of the second part of the first member and extends away from the first center axis of the first hole to accommodate a projection of the second connection portion of the second plate member, wherein a first part of the second connection portion of the second member comprises a wall that extends around and faces away from the second center axis of the second hole, wherein the projection of the second member extends away from the wall of the first part of the second member to form a first free end of the second member, wherein a second part of the second connection portion of the second member comprises a wall that is spaced apart from the second hole and that extends around and faces towards the second center axis of the second hole, and wherein a groove is formed in the wall of the second part of the second plate member and extends away from the second center axis of the second hole to accommodate the projection of the first connection portion of the first plate member, wherein the projection of the first plate member is inserted into the groove of the second plate member and the projection of the second plate member is inserted into the groove of the first plate member;
a bone anchor having a head and a shaft, the shaft insertable through the first and second holes until the head seats within the second hole; and
a cover member disposed in the first hole and over the head of the bone anchor to prevent release of the bone anchor and decoupling of the first and second plate members relative to each other while the cover member is so disposed.

2. The modular bone plate system according to claim 1, wherein the first hole is threaded, and the cover member is threadedly engaged in the first hole.

3. A modular bone plate system comprising:
a first plate member having a first circular screw hole and defining a first projection and first groove;
a second plate member having a second circular screw hole and defining a second projection and second groove, at least one of the first and second screw circular holes having threads; and
a set screw separable from the first and second plate members and having a non-threaded head enlarged in diameter relative to a threaded shaft, wherein the first plate member is assembled relative to the second plate member such that the first projection resides in the second groove and the second projection resides in the first groove, and the first and second screw circular holes are aligned, and the threaded shaft of the set screw is removably threadedly engaged with at least one of the first and second circular screw holes.

4. A modular bone plate system comprising:

a first plate member having a top surface defining a top plane, a bottom surface defining a bottom plane, a first circular screw hole having a first central axis intersecting the top and bottom planes, and defining a first ring-shaped projection and first groove;

a second plate member having a top surface defining a top plane, a bottom surface defining a bottom plane, a second circular screw hole having a second central axis intersecting the top and bottom planes of the second plate member, and defining a second ring-shaped projection and second groove;

a first connector; and a second connector, wherein the first plate member is assembled relative to the second plate member such that the first ring-shaped projection resides in the second groove and the second ring-shaped projection resides in the first groove in overlying arrangement with the first ring-shaped projection, and the first and second connector are together assembled along a common axis through the first and second circular screw holes from a top surface of the first plate member and a bottom surface of the second plate member.

5. The modular bone plate system according to claim 4, wherein the first connector is a nut and the second connector is a screw.

6. The modular bone plate system according to claim 4, wherein the first connector extends from the top surface of the first plate member through the first circular screw hole and at least a portion of the second circular screw hole, and the second connector extends from the bottom surface of the second plate member and at least a portion of the second circular screw hole.

7. A modular bone plate system comprising:

a first plate member comprising a top surface defining a top plane, a bottom surface defining a bottom plane, and a first connection portion defining a first hole with a first center axis that intersects the top plane and the bottom plane, wherein the first connection portion of the first plate member comprises a wall that is spaced apart from the first hole and has a first wall portion that extends around and faces towards the first center axis of the first hole, and second and third wall portions on opposite sides of the first hole that extend transverse to the first hole, and wherein a groove extends in the first, second, and third wall portions, the first hole at least partially provided in a first convex portion that projects outward and beyond the first, second and third wall portions; and a second plate member comprising a top surface defining a top plane and a bottom surface defining a bottom plane, and a second connection portion defines a second hole with a second center axis that intersects the top and bottom planes of the second plate member, a first part of the second connection portion of the second plate member comprises a projection that is adapted to be received in the groove of each of the first, second and third wall portions of the first connection portion of the first plate member, the second hole at least partially provided in a second convex portion, the first and second convex portions adapted to extend past each other when the projection is received in the groove of each of the first, second and third wall portions.

8. The modular bone plate system according to claim 7, wherein the first wall portion is curved, and the second and third wall portions are straight.

9. The modular bone plate system according to claim 7, wherein the second and third wall portions both extend parallel to a diameter of the first hole.

10. The modular bone plate system according to claim 7, wherein the first and second plate members define a longitudinal axis, and the second and third wall portions are oriented orthogonal to the longitudinal axis.

11. The modular bone plate system according to claim 7, wherein the plate system has a maximum width, and the projection of the second member and the groove extending along the first, second and third portions of the wall of the first plate member are provided at the maximum width of the plate system.

* * * * *